United States Patent
Kosuge et al.

(10) Patent No.: US 8,729,541 B2
(45) Date of Patent: May 20, 2014

(54) PHENANTHRENE COMPOUND AND ORGANIC LIGHT EMITTING DEVICE USING THE SAME

(75) Inventors: Tetsuya Kosuge, Yokohama (JP); Jun Kamatani, Tokyo (JP); Hiroyuki Tomono, Numazu (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/880,250

(22) PCT Filed: Oct. 25, 2011

(86) PCT No.: PCT/JP2011/075016
§ 371 (c)(1),
(2), (4) Date: Apr. 18, 2013

(87) PCT Pub. No.: WO2012/060307
PCT Pub. Date: May 10, 2012

(65) Prior Publication Data
US 2013/0207096 A1    Aug. 15, 2013

(30) Foreign Application Priority Data
Nov. 5, 2010    (JP) .................................. 2010-248352

(51) Int. Cl.
*H01L 51/00*    (2006.01)
(52) U.S. Cl.
USPC .................... 257/40; 438/99; 257/E51.022
(58) Field of Classification Search
USPC .................. 257/40, 642, E25.008, E51.003, 257/E51.022; 438/82, 99
See application file for complete search history.

(56) References Cited

U.S. PATENT DOCUMENTS 5,843,606 A * 12/1998 Miyamoto et al. ........... 430/58.5

FOREIGN PATENT DOCUMENTS

| JP | 2009-51764 A | 3/2009 |
|---|---|---|
| JP | 2009-215333 A | 9/2009 |
| JP | 2009-221442 A | 10/2009 |
| WO | 2006/130598 A2 | 12/2006 |
| WO | 2009/100925 A1 | 8/2009 |
| WO | 2010/002850 A1 | 1/2010 |

* cited by examiner

*Primary Examiner* — Quoc Hoang
(74) *Attorney, Agent, or Firm* — Fitzpatrick, Cella, Harper & Scinto

(57) ABSTRACT

The present invention provides an organic light emitting device having high light emission efficiency. The organic light emitting device includes an anode, a cathode and an organic compound layer which is sandwiched between the anode and the cathode, wherein the organic compound layer contains a phenanthrene compound represented by the following general formula [1]:

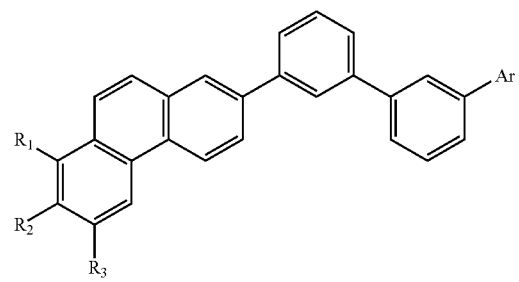

[1]

wherein $R_1$ to $R_3$ each represent a hydrogen atom or an alkyl group having 1 to 4 carbon atoms; and Ar is a substituent selected from any in the group consisting of aryl groups represented by the following formulae [2a] to [2h]:
[2a]
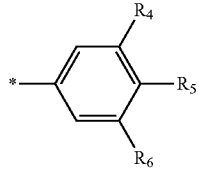
[2b]
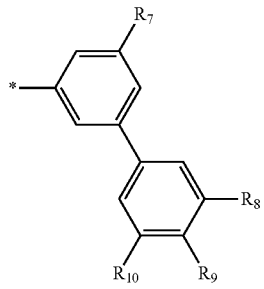
[2c]
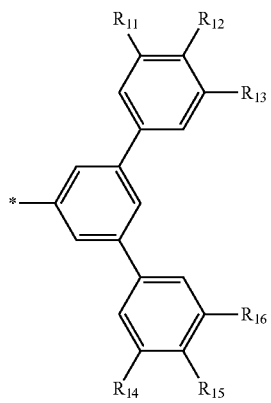
-continued
[2d]
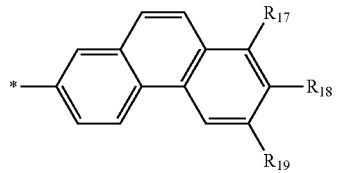
[2e]
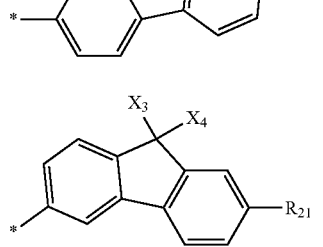
[2f]
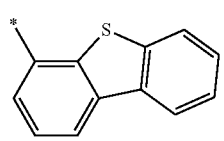
[2g]
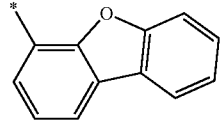
[2h]
10 Claims, 1 Drawing Sheet

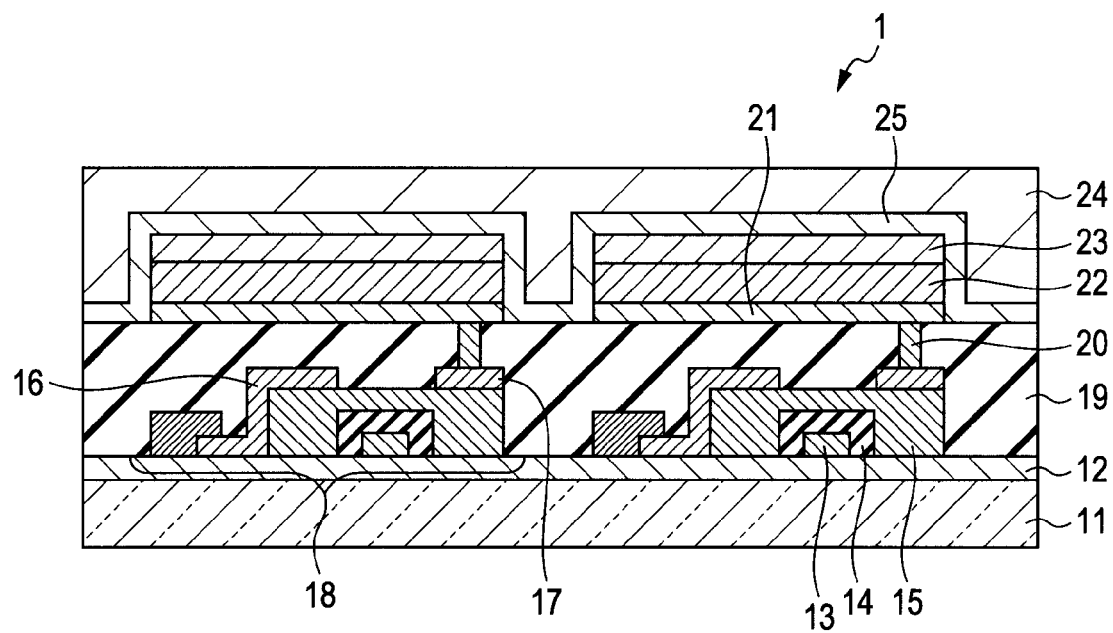

PHENANTHRENE COMPOUND AND ORGANIC LIGHT EMITTING DEVICE USING THE SAME

TECHNICAL FIELD

The present invention relates to a phenanthrene compound, and an organic light emitting device using the same.

BACKGROUND ART

The organic light emitting device is an electronic device having an anode, a cathode and an organic compound layer arranged between both these electrodes. When an exciton generated by the recombination of a hole and an electron injected from the electrodes respectively, which occurs in the organic compound layer, particularly in a light emitting layer, returns to a ground state, the organic light emitting device emits light.

The recent organic light emitting device has remarkably advanced, and is characterized in that this organic light emitting device allows a thin and lightweight organic light emitting device which has low driving voltage, various emission wavelengths and rapid response to be produced.

By the way, the organic light emitting device is roughly classified into a fluorescent light emitting device and a phosphorescent light emitting device according to the type of the exciton associated with light emission. In the phosphorescent light emitting device out of the devices, a triplet exciton participates in light emission, and the phosphorescent light emitting device is an electronic device having a phosphorescent light emitting material in an organic compound layer constituting the organic light emitting device, specifically, in the light emitting layer. Here, the phosphorescent light emitting material is excited to a triplet state by the recombination of the positive hole and the electron, and emits phosphorescence when returning to the ground state. For this reason, the phosphorescent light emitting device is an organic light emitting device which emits light originating from this triplet exciton.

By the way, the internal quantum yield of the phosphorescent light emitting device is theoretically four times the internal quantum yield of the fluorescent light emitting device, and accordingly the phosphorescent light emitting device has received attention in resent years. However, there is still room for improvement in the light emission efficiency of the phosphorescent light emitting device.

On the other hand, various materials to be used for the phosphorescent light emitting device have been proposed. For example, a compound H01 represented by the following formula is proposed as a host of the phosphorescent light emitting layer (see Patent document 1).

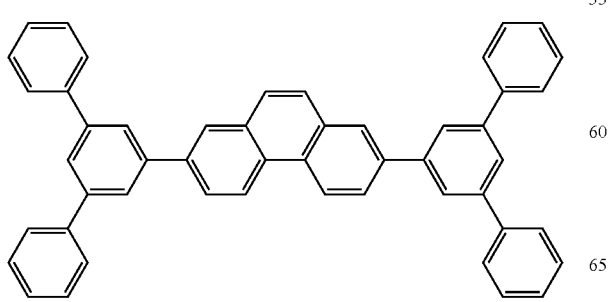

H01

CITATION LIST

Patent Literature

Japanese Patent Application Laid-Open No. 2009-215333 (no corresponding foreign application)

SUMMARY OF INVENTION

However, the above described compound H01 has an energy in the minimum excitation triplet state ($T_1$ energy) as low as 480 nm in terms of wavelength, and has a shallow LUMO level of −2.82 eV (low electron affinity). Here, it is necessary to make the LUMO level further deep, from the viewpoint of light emission efficiency.

The present invention has been made in order to solve the above described problem, and an object of the present invention is to provide an organic light emitting device having high light emission efficiency.

A phenanthrene compound is characterized in that the compound is represented by the following general formula [1]:

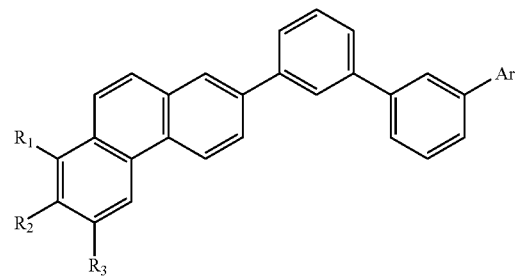

[1]

wherein $R_1$ to $R_3$ each represent a hydrogen atom or an alkyl group having 1 to 4 carbon atoms; and Ar is a substituent selected from any in the group consisting of aryl groups represented by the following formulae [2a] to [2h]:

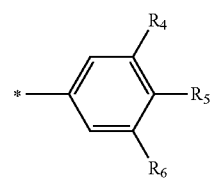

[2a]

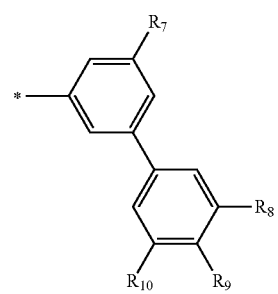

[2b]

-continued

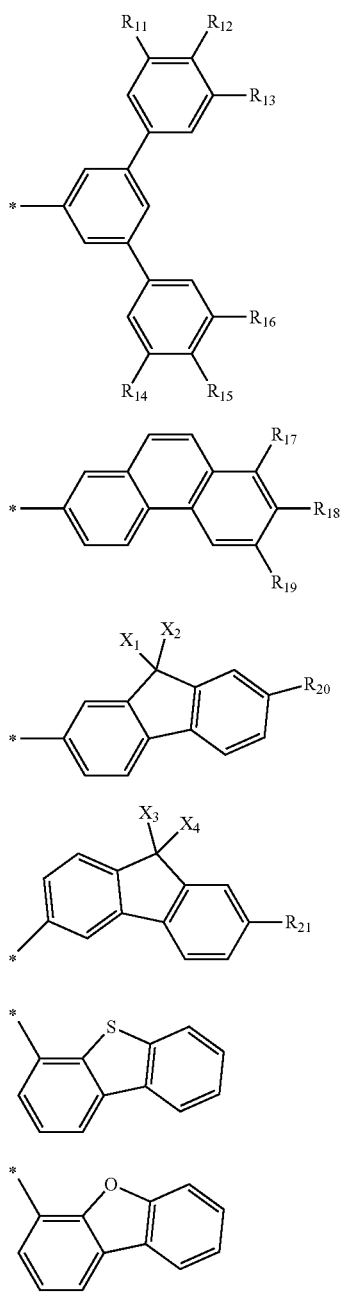

wherein in formulae [2a] to [2f], $R_4$ to $R_{21}$ each represent a hydrogen atom or an alkyl group having 1 to 4 carbon atoms; in formulae [2e] and [2f], $X_1$ to $X_4$ each represent a hydrogen atom or an alkyl group having 1 to 4 carbon atoms; and in formulae [2a] to [2h], * represents a bond.

The present invention can provide an organic light emitting device having high light emission efficiency.

Further features of the present invention will become apparent from the following description of exemplary embodiments with reference to the attached drawing.

BRIEF DESCRIPTION OF DRAWING

FIGURE is a schematic sectional view illustrating an example of a display unit using an organic light emitting device according to the present invention.

DESCRIPTION OF EMBODIMENTS

The phenanthrene compound according to the present invention is a compound represented by the following general formula [1].

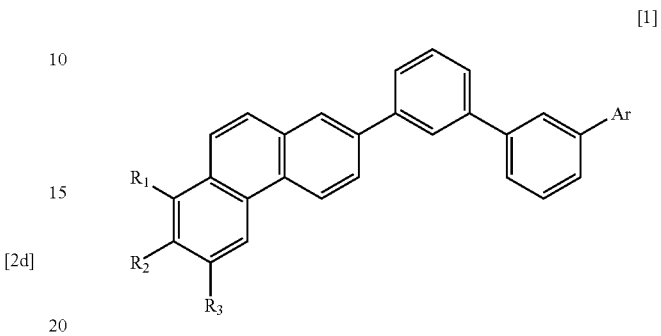

In formula [1], $R_1$ to $R_3$ each represent a hydrogen atom or an alkyl group having 1 to 4 carbon atoms.

The alkyl group represented by $R_1$ to $R_3$ includes a methyl group, an ethyl group, an n-propyl group, an iso-propyl group, an n-butyl group, an iso-butyl group, a sec-butyl group and a tert-butyl group.

The above described alkyl group may further have a substituent. The above described alkyl group is optionally further substituted, for instance, by: a hydrocarbon aromatic ring group such as a phenyl group, a naphthyl group, a phenanthryl group and a fluorenyl group; a heteroaromatic ring group such as a thienyl group, a pyrrolyl group and a pyridyl group; a substituted amino group such as a dimethylamino group, a diethylamino group, a dibenzylamino group, a diphenylamino group, a ditolylamino group and a dianisolylamino group; an alkoxy group such as a methoxy group and an ethoxy group; an aryloxy group such as a phenoxy group and a naphthoxy group; a halogen atom such as fluorine, chlorine, bromine and iodine; a hydroxy group; a cyano group; and a nitro group.

In formula [1], Ar is a substituent selected from any in the group consisting of aryl groups represented by the following formulae [2a] to [2h].

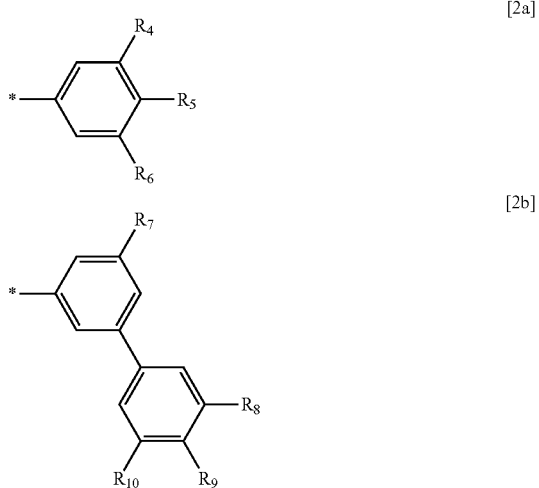

-continued

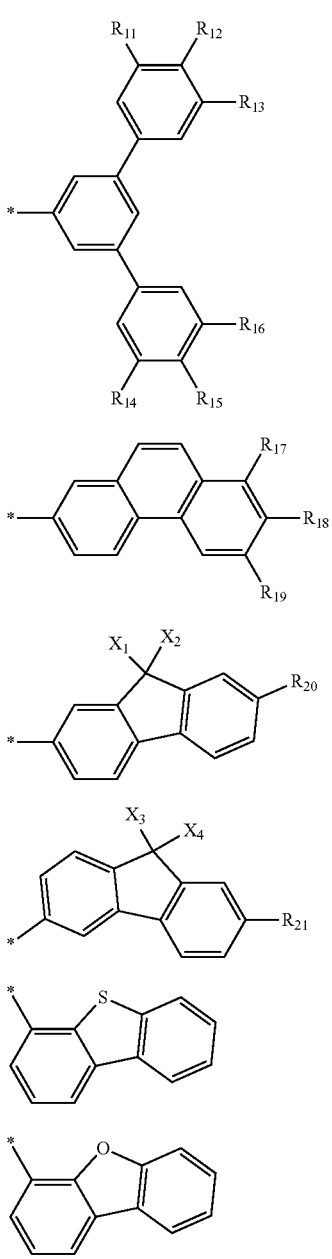

In formulae [2a] to [2f], $R_4$ to $R_{21}$ each represent a hydrogen atom or an alkyl group having 1 to 4 carbon atoms. In addition, specific examples of the alkyl group represented by $R_4$ to $R_{21}$ are the same as the specific examples of the alkyl group represented by $R_1$ to $R_3$ in formula [1].

In formulae [2e] to [2f], $X_1$ to $X_4$ each represent a hydrogen atom or an alkyl group having 1 to 4 carbon atoms. In addition, specific examples of the alkyl group represented by $X_1$ to $X_4$ are the same as the specific examples of the alkyl group represented by $R_1$ to $R_3$ in formula [1].

In formulae [2a] to [2h], * represents a bond, and specifically represents a position to be bonded to a phenanthrene-biphenyl skeleton included in the compound of formula [1].

Next, a method for synthesizing the phenanthrene compound according to the present invention will be described below.

The phenanthrene compound according to the present invention can be divided into a phenanthrene unit, an m-biphenylene linking group and an aryl group, as shown below.

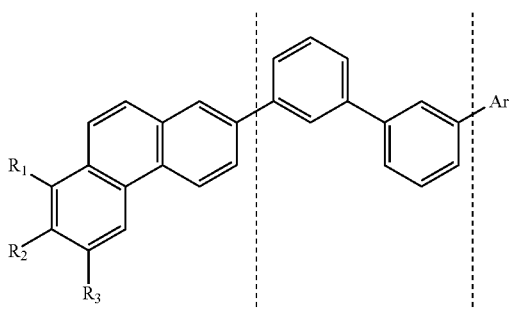

Phenanthrene Unit
m-Biphenylene Linking Group
Aryl Group

Based on the structural characteristics, the phenanthrene compound according to the present invention is synthesized, for instance, by using a synthetic scheme which is shown below. Incidentally, in the following synthetic scheme, Ar is an aryl group represented by any one of formulae [2a] to [2h], and $R_1$ to $R_3$ each represent a hydrogen atom or an alkyl group having 1 to 4 carbon atoms.

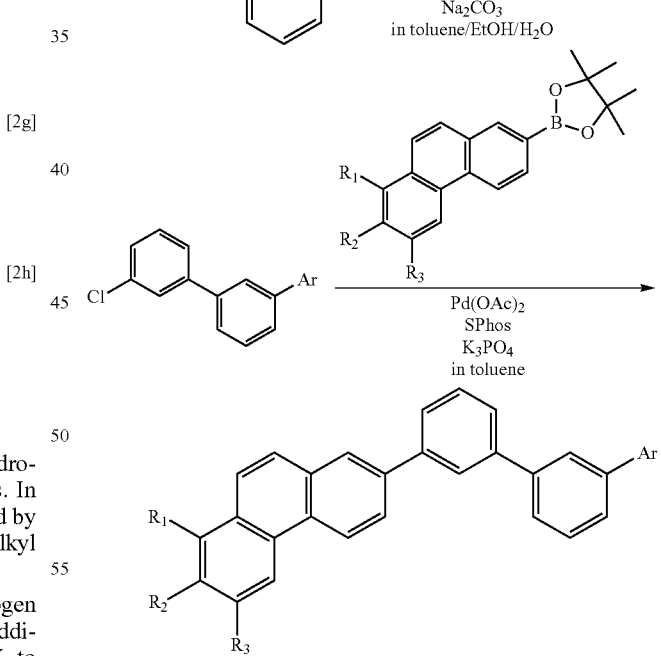

The above described synthetic scheme is a process for sequentially reacting compounds which are bases of the aryl group and a phenanthrene unit with a compound (3-bromo-3'-chlorobiphenyl) which is a base of the m-biphenylene linking group by using a coupling reaction with a Pd catalyst. The phenanthrene compound according to the present invention is synthesized, for instance, through the following steps (a) to (b).

Step (a): the step of conducting a coupling reaction of 3-bromo-3'-chlorobiphenyl with a derivative of a boronate, which becomes a base of an aryl group (Ar—), by a Pd catalyst Step (b): the step of conducting a coupling reaction of the compound obtained in the step (a) with a derivative of a pinacol boronic acid ester, which becomes a base of a phenanthrene unit, by a Pd catalyst In addition, in the above described synthetic scheme, Ar and R can be each appropriately selected within a range of the scope of the present invention, and a desired phenanthrene compound can be synthesized.

When the phenanthrene compound according to the present invention is used as a material constituting an organic light emitting device, the phenanthrene compound can be purified by sublimation as a purification step right before the use. The reason is because the sublimation purification has a great effect in highly purifying an organic compound among the techniques for highly purifying the organic compound. Here, when the compound is purified by sublimation, as the molecular weight of the target organic compound is higher, a higher temperature is needed, in general. Because of this, when an organic compound with a high molecular weight is purified by sublimation, the organic compound tends to cause thermal decomposition due to the high temperature, and the like. Accordingly, the molecular weight of the organic compound to be used as a material constituting the organic light emitting device can be 1,000 or less, from such a viewpoint that the organic compound should be capable of being purified by sublimation without being excessively heated.

As was described above, the phenanthrene compound according to the present invention can be divided into a phenanthrene unit, an m-biphenylene linking group and an aryl group.

In the phenanthrene compound according to the present invention, the phenanthrene unit is a main skeleton, the aryl group is an auxiliary skeleton, and the m-biphenylene linking group (3,3'-biphenylene group (m-biphenylene group)) links the main skeleton with the auxiliary skeleton.

The phenanthrene unit which is the main skeleton is a central partial structure in the phenanthrene compound according to the present invention, and becomes a partial structure which determines physical property values such as $S_1$ energy, $T_1$ energy, a HOMO level and a LUMO level of the whole of the compound. In contrast to this, the aryl group which is the auxiliary skeleton is an ancillary attributive partial structure in the phenanthrene compound according to the present invention, and becomes a partial structure which is used for finely adjusting the physical property values of the whole of the above described compound.

First, characteristics of the phenanthrene unit which is the main skeleton will be described below. The following Table 1 is a table showing $T_1$ energy, $S_1$ energy and LUMO levels of main aromatic compounds. For information, in Table 1, the $T_1$ energy and the $S_1$ energy are values which have been converted into a wavelength, and the LUMO level is a calculated value.

TABLE 1

| Compound name | Structural formula | $T_1$ [nm] | $S_1$ [nm] | LUMO [eV] |
|---|---|---|---|---|
| Benzene | 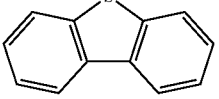 | 339 | 260 | +0.10 |

TABLE 1-continued

| Compound name | Structural formula | $T_1$ [nm] | $S_1$ [nm] | LUMO [eV] |
|---|---|---|---|---|
| Dibenzo-thiophene | 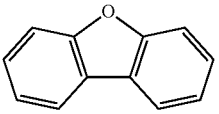 [SMILES: c1ccc2c(c1)oc1ccccc12] | 415 | 326 | −0.95 |
| Dibenzo-furan | 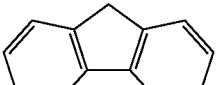 | 417 | 301 | −0.92 |
| Fluorene | 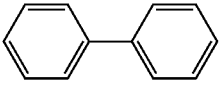 | 422 | 301 | −0.71 |
| Biphenyl | 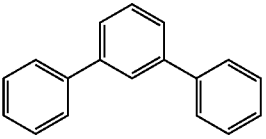 [SMILES: c1ccc(-c2cccc(-c3ccccc3)c2)cc1] | 436 | 306 | −0.67 |
| m-Terphenyl | 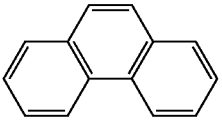 [SMILES: c1ccc2c(c1)ccc1ccccc12] | 445 | 304 | −0.82 |
| Phenan-threne | 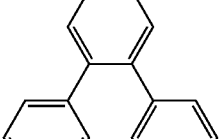 | 459 | 347 | −0.99 |
| o-Terphenyl |  | 464 | — | −0.72 |
| Naphthalene | 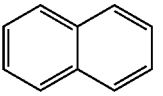 | 472 | 311 | −0.96 |
| p-Terphenyl | 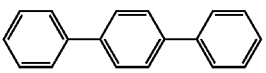 | 490 | 311 | −1.02 |
| Chrysene | 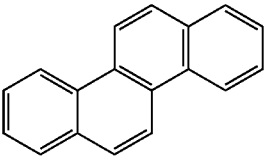 [SMILES: c1ccc2c(c1)ccc1c3ccccc3ccc21] | 500 | 360 | −1.27 |

According to Table 1, phenanthrene has such characteristics that the $T_1$ energy is higher but on the other hand, the $S_1$ energy is lower than that of the other compounds, and the LUMO level is deepest in aromatic compounds having equivalent $T_1$ energy.

The present inventors thought that the compound which has the phenanthrene unit as the main skeleton was suitable for a host of a light emitting layer of an organic light emitting device which emits phosphorescence, from the above described characteristics of the phenanthrene and reasons which will be described later.

Generally, in the phosphorescent light emitting device, the $T_1$ energy of the host needs to be set so as to be higher than the $T_1$ energy of a guest (phosphorescent light emitting material), in order to prevent the light emission efficiency from being lowered due to non-radiative deactivation from the $T_1$ of the host.

For instance, in the phosphorescent light emitting device (green phosphorescent light emitting device) having a green light as an emission color, the $T_1$ energy of the host needs to be controlled to 490 nm or less in terms of a wavelength so as to be sufficiently higher than the $T_1$ energy of the light emitting material. Here, in consideration of the $T_1$ energy of a sole phenanthrene ring, the $T_1$ energy of the compound having the phenanthrene unit as the main skeleton is 480 nm or less at lowest in terms of a wavelength. This value satisfies the above described condition for the host. Accordingly, when the compound having the phenanthrene unit as the main skeleton is used as the host of the light emitting layer, the light emission efficiency of the device is enhanced.

On the other hand, in the phosphorescent light emitting device, it is better to make the $S_1$ energy of the host of the light emitting layer as low as possible. By making the $S_1$ energy of the host low, the level difference (hereafter referred to as energy gap) between the HOMO level and the LUMO level of the host itself can be made small. In addition, the low $S_1$ energy of the host usually means that the LUMO level of the host is deep, except for the case that the HOMO level of the host itself is extremely shallow.

When the compound having the deep LUMO level is used as the host of the light emitting layer in the phosphorescent light emitting device, a barrier of electron injection from an electron transporting layer or a hole blocking layer which is adjacent in the cathode side of the light emitting layer is lowered, and accordingly a performance of injecting an electron into the light emitting layer is enhanced. At this time, a carrier recombination region in the light emitting layer, in other words, a light emitting region is expanded to the inner part of the light emitting layer, and the center of the distribution of the light emitting region becomes to be positioned in the central part of the light emitting layer. Thereby, a local light emission which can occur in the interface between the light emitting layer and the electron transporting layer or the hole blocking layer is suppressed, and accordingly it can be prevented that the light emission efficiency is lowered by exciton leakage and the like.

Generally, when a high $T_1$ energy of the compound which becomes the host of the light emitting layer is preferentially secured in the phosphorescent light emitting device, the $S_1$ energy of the compound becomes very high (in other words, the energy gap becomes very large), and accordingly the LUMO level often becomes quite shallow. In contrast to this, in the compound having the phenanthrene unit as the main skeleton, the high $T_1$ energy and the low $S_1$ energy (deep LUMO level) can be compatible. Accordingly, by using the compound having the phenanthrene unit as the main skeleton according to the present invention as the host of the light emitting layer, the light emission efficiency of the device is enhanced.

However, as was described above, when the HOMO level is extremely shallow, the LUMO level does not become deep so much even though the $S_1$ energy of the compound is low. However, according to Table 1, it is shown that the LUMO level of the phenanthrene is the deepest in the aromatic compounds having the equivalent $T_1$ energy. Accordingly, the phenanthrene compound having the phenanthrene unit as the main skeleton according to the present invention has a tendency that the LUMO level becomes deep, and accordingly can enhance the light emission efficiency of the device by being introduced into the light emitting layer as the host.

Next, an aryl group (—Ar) which is an auxiliary skeleton will be described below.

The phenanthrene unit which is the main skeleton of the phenanthrene compound according to the present invention has characteristics that $T_1$ energy is high but $S_1$ energy is low, and a LUMO level is deepest in the aromatic compounds having the equivalent $T_1$ energy, as was described above. However, it is impractical to use the phenanthrene itself as a material constituting the organic light emitting device in an as-unsubstituted state. The reason is because the phenanthrene itself has high crystallinity and a stable amorphous film cannot be obtained therefrom. Then, it is necessary to introduce some auxiliary skeleton into the phenanthrene unit which is the main skeleton. Here, the unit or the substituent which becomes the auxiliary skeleton needs to be a unit or a substituent which has higher Si energy and $T_1$ energy than those of the phenanthrene unit which is the main skeleton, as its condition. Here, in consideration of Table 1, the auxiliary skeletons worthy of being introduced into the phenanthrene unit which is the main skeleton are seven types which are benzene, dibenzothiophene, dibenzofuran, fluorene, biphenyl, m-terphenyl and phenanthrene. In addition, a phenanthrene ring different from the phenanthrene unit which is the main skeleton may also be introduced as the auxiliary skeleton. In this case, the introduced phenanthrene ring also functions as the main skeleton.

However, one part of the above described seven types of auxiliary skeletons occasionally makes the $T_1$ energy of the whole of the compound greatly lower or occasionally makes the $S_1$ energy greatly increase, depending on its substitution position. Here, considering also the form (position of a bond) of being introduced into the main skeleton, the Ar which is the auxiliary skeleton is eight types of aryl groups which are represented by the following formulae [2a] to [2h].

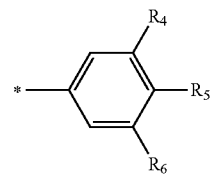

[2a]

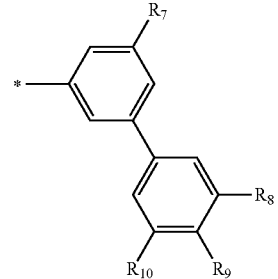

[2b]

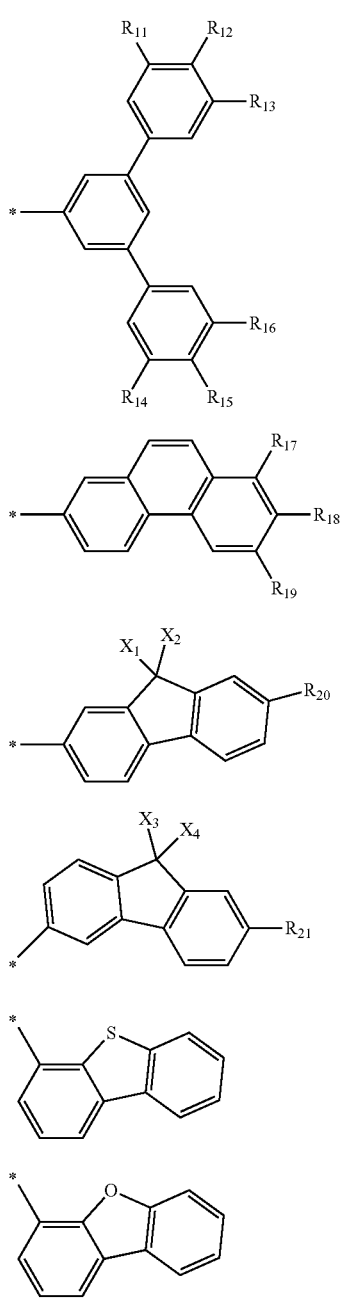

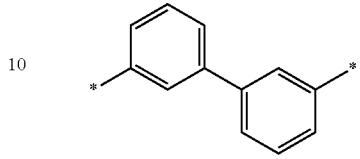

m-Biphenylene Group

The m-biphenylene group is the linking group in which the position of the bond (bonding position) is designated, among biphenylene groups, as was shown above. The reason why the position of the bond (bonding position) is designated in the m-biphenylene group is because by being linked at these positions, the biphenylene group cuts the π-conjugation of the whole compound with a bond (the bond which combines the benzene rings constituting the m-biphenylene group with each other) located at the center in the m-biphenylene group. As a result, the $T_1$ energy in the whole of the compound is determined by a portion at "phenanthrene-benzene" having the $T_1$ energy lower than that of a portion at an "auxiliary skeleton-benzene", and does not greatly decrease from the $T_1$ energy of the phenanthrene unit which is the main skeleton.

It is considered that a 1,3-phenylene group (m-phenylene group) is also a linking group having the same effect, but it is known from Table 1 that the m-biphenylene group has a deeper LUMO level than that of the 1,3-phenylene group (m-phenylene group). In addition, as was described above, it is desirable to deepen the LUMO level in the phenanthrene compound according to the present invention, and accordingly the m-biphenylene group is more desirable.

Next, the bonding position between the main skeleton (phenanthrene skeleton) and the linking group (m-biphenylene group) will be described below. In the phenanthrene compound according to the present invention, its phenanthrene skeleton is substituted by the m-biphenylene group on the carbon atom at the 2-position thereof. This reason will be described below.

The number of the substitution position of the phenanthrene will be shown below.

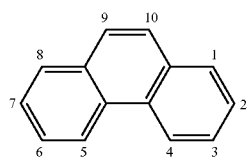

Compounds having a phenanthrene skeleton substituted by a phenyl group have different physical properties ($T_1$ energy and the like) of the compound itself according to the substitution position of the phenyl group. The following Table 2 shows the $S_1$ energy, the $T_1$ energy, the energy difference (ΔS–T) between the $S_1$ energy and the $T_1$ energy, and the dihedral angle formed by the phenanthrene ring and the benzene ring of compounds whose phenanthrene skeleton is substituted by a phenyl group(s) at respective predetermined Next, the m-biphenylene linking group will be described below.

Among the above described eight types of the auxiliary skeletons, four types of the substituents that are a dibenzothiophenyl group, a dibenzofuranyl group, a fluorenyl group and a phenanthryl group which are condensation polycyclic groups cannot be directly bonded to the phenanthrene unit which is the main skeleton. The reason is because the length of π-conjugation of the whole compound is excessively expanded by the formation of this bond, the $T_1$ energy is remarkably lowered, and the compound cannot maintain the high $T_1$ energy originating from the phenanthrene skeleton.

In order to prevent the lowering of this $T_1$ energy, the phenanthrene compound according to the present invention positions thereof. For information, Table 2 is a calculation result obtained by optimizing the structure by molecular orbital calculation.

TABLE 2

| Substitution position | Structural formula | $S_1$ [nm] | $T_1$ [nm] | Δ S-T [nm] | Dihedral angle [°] |
|---|---|---|---|---|---|
| 1-Position | | 315 | 462 | 147 | 55.8 |
| 2-Position | | 323 | 461 | 138 | 37.1 |
| 3-Position | | 319 | 471 | 152 | 38.0 |
| 4-Position | | 311 | 455 | 144 | 78.8 |
| 9-Position | | 315 | 465 | 150 | 55.8 |
| 2- and 7-Positions | | 334 | 472 | 138 | 37.8 |

First, the phenyl phenanthrenes whose phenanthrene skeleton is substituted by one phenyl group are compared. Then, it is clear that 2-phenyl phenanthrene (2-position substitution product) has the lowest $S_1$ energy and the highest $T_1$ energy, and consequently has smaller ΔS–T than other substitution products. The reason why the $S_1$ energy of the 2-position substitution product is low is because the dihedral angle formed by a phenanthrene ring and a benzene ring is the smallest, and thereby the π-conjugation is moderately widened. Accordingly, in the phenanthrene compound according to the present invention, carbon at the 2-position of the phenanthrene unit which is the main skeleton can be bonded to the m-biphenylene group to allow the above described characteristics of the phenanthrene unit to be most strongly reflected in the whole physical properties of the compound.

However, in a compound having this 2-phenyl phenanthrene substituted by another phenyl group, for instance, 2,7-diphenyl phenanthrene, the $T_1$ energy greatly decreases compared to that of 2-phenyl phenanthrene.

In consideration of the above description, it can be said that when the m-biphenylene group is bonded to the phenanthrene unit while taking the advantage of the characteristics of the phenanthrene unit which is the main skeleton, only one m-biphenylene group ought to be bonded at the 2-position of the phenanthrene skeleton.

In addition, the phenanthrene compound according to the present invention may have also the alkyl group introduced into the phenanthrene unit which constitutes the compound and the aryl group. Specifically, the alkyl group may be also introduced into any position of $R_1$ to $R_{21}$ shown by formulae [1] and [2a] to [2f]. Because a distance between compounds (distance between molecules) in an amorphous film state can be increased by the excluded volume effect of the alkyl group, the carrier mobility can be adjusted to be low. In addition, by introducing the alkyl group into the compound, the solubility of the compound itself into an organic solvent can be enhanced.

By the way, the positions of $R_1$ to $R_{21}$ shown by formulae [1] and [2a] to [2f] are positions which do not almost give influence on the $S_1$ energy and the $T_1$ energy of the compound itself even if the alkyl group is introduced into the respective positions. In other words, even if the alkyl group is introduced into the respective positions of $R_1$ to $R_{21}$ shown by formulae [1] and [2a] to [2f], the introduced alkyl group does not almost give influence on the conformation of the phenanthrene compound according to the present invention. The conformation described here means the distortion of the bond around the axis of the aryl-aryl bond in the compound, in other words, the size of the dihedral angle between two aromatic rings which are bonded by the aryl-aryl bond. When the conformation changes and the dihedral angle increases, the $S_1$ energy of the compound also consequently increases. However, in the present invention, the conformation of the phenanthrene compound according to the present invention is not distorted by the alkyl group which can be introduced, the dihedral angle in each aryl-aryl bond does not increase, and accordingly the $S_1$ energy of the compound itself does not increase.

In addition, even though the alkyl group is introduced into respective positions of $R_1$ to $R_{21}$, the planar structure of the aromatic ring is not distorted and the chemical stability of the aromatic ring is not lowered. For instance, when the alkyl group is introduced into the 5-position of the phenanthrene skeleton, the steric repulsion of this alkyl group against a hydrogen atom bonded to a carbon atom at the 4-position becomes large, and the phenanthrene ring itself is distorted. Then, when the position to which the alkyl group is introduced is designated to the 6-position, the 7-position and the 8-position (positions when the bonding position to the m-biphenylene group is designated to be the 2-position) of the phenanthrene skeleton, as in the phenanthrene compound according to the present invention, the above described steric repulsion does not occur, and accordingly the chemical stability is not lowered.

As was described above, the phenanthrene compound according to the present invention is a compound having high $T_1$ energy and a deep LUMO level due to the specific molecular structure.

Specific examples of the phenanthrene compound according to the present invention will be described below. However, the present invention is not limited to the specific examples.

A01

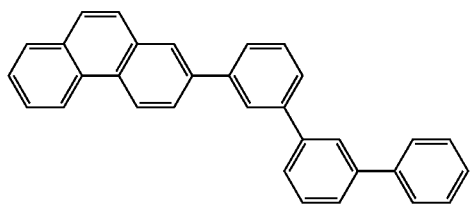

A02

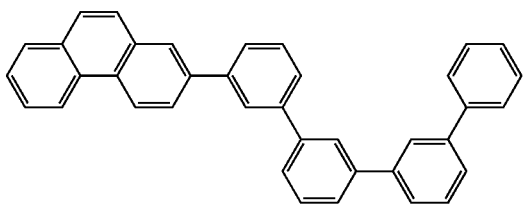

A03

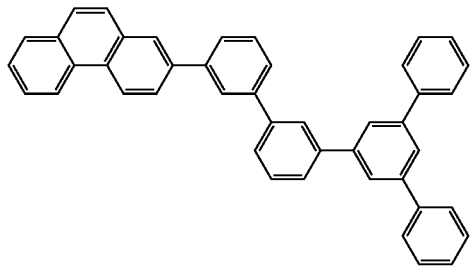

A04

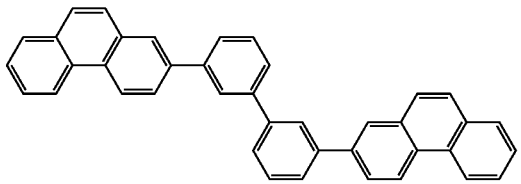

A05

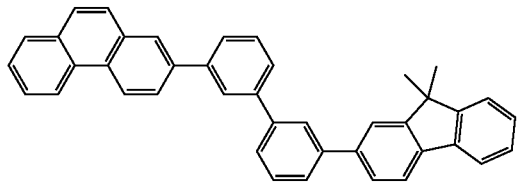

A06

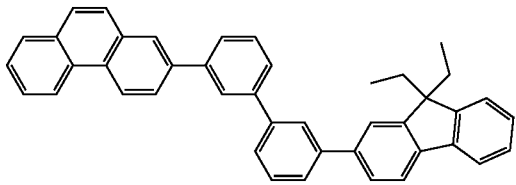

A07

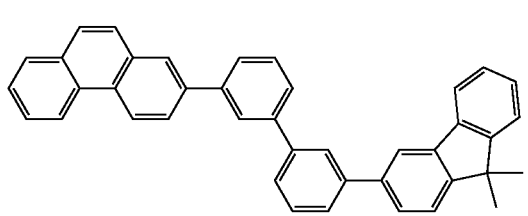

A08

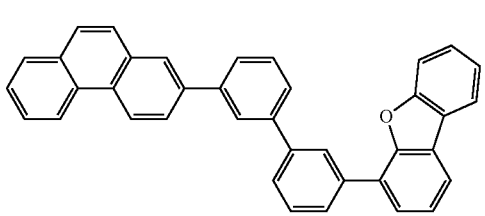

-continued
A09
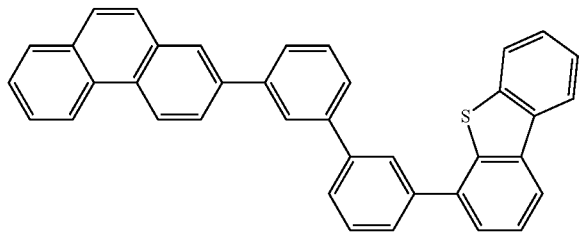
B01
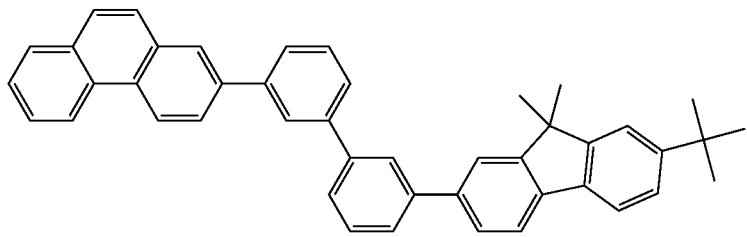
B02  B03
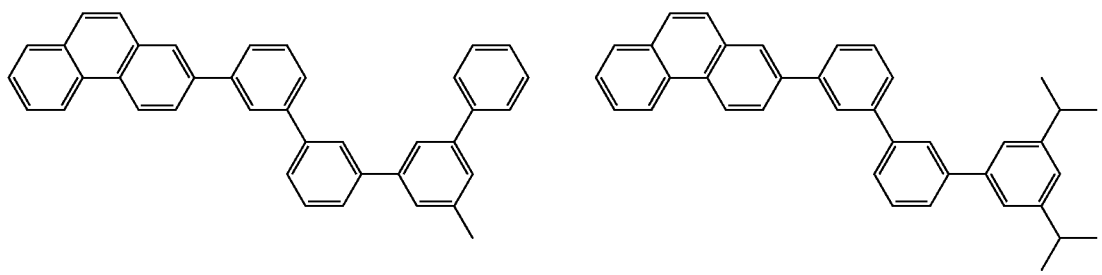
B04  B05
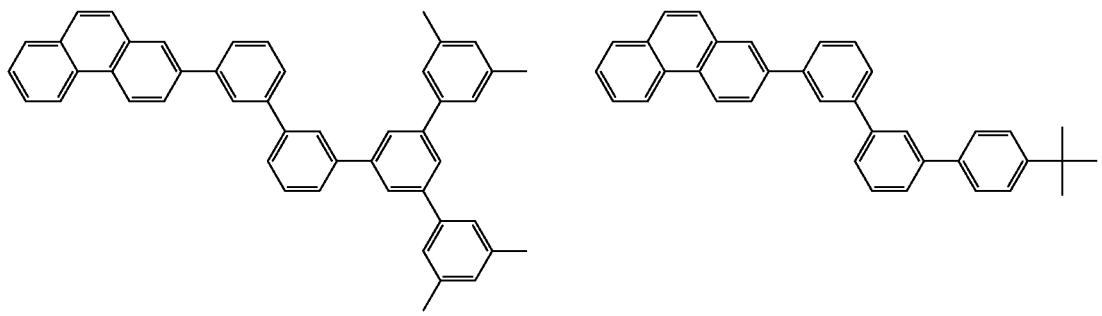
B06
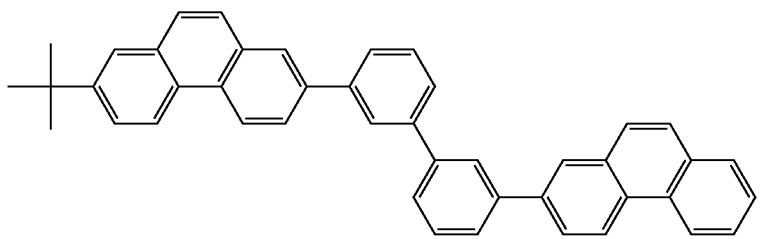
B07  B08
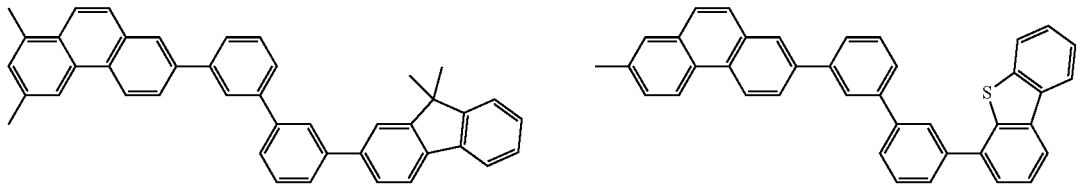

-continued

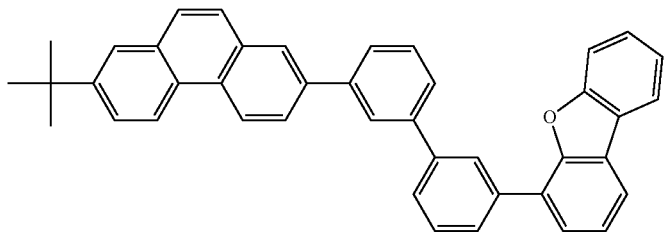
B09

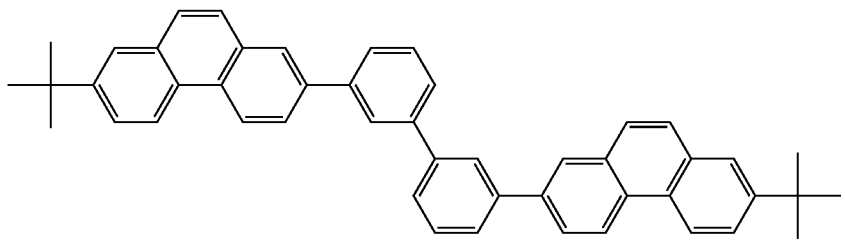
B10

Among the above described exemplified compounds, the compounds belonging to group A are compounds in which all the substituents represented by $R_1$ to $R_{21}$ shown in formula [1] and formula [2a] to formula [2f] are hydrogen atoms.

These compounds in group A have no alkyl substituent which acts as an electron-donating group in the molecule, except for an alkyl group by which the fluorene skeleton can be substituted at the 9-position thereof. Accordingly, the compound in group A is a compound which has a deeper LUMO level among the phenanthrene compounds according to the present invention. For this reason, when the compound in group A is used as a host of the light emitting layer, the efficiency of electron injection into the light emitting layer is further enhanced, and accordingly the light emission efficiency of the device can be further increased.

Among the above described exemplified compounds, the compounds belonging to group B are compounds in which any of substituents represented by $R_1$ to $R_{21}$ shown in a formula [1] and formulae [2a] to formula [2f] is substituted by an alkyl group having 1 to 4 carbon atoms. The solubility of the compound itself is enhanced depending on the number and the type of the substituting alkyl groups, and accordingly the compounds belonging to group B are effective when it is intended to enhance the handleability of the material or produce an organic light emitting device by wet-process. In addition, due to the excluded volume effect of the alkyl group, a distance between molecules of the compound itself increases in the amorphous state. Because of this, the compound belonging to group B is a material of which the carrier mobility is lower. Similarly to the compounds in group A, the compounds in group B are used as the host of the light emitting layer, but are particularly useful when it is desired to lower the carrier mobility in the light emitting layer.

Next, the organic light emitting device according to the present invention will be described below. The organic light emitting device according to the present invention includes: an anode and a cathode which are a pair of electrodes that confront each other; and an organic compound layer which is sandwiched between the anode and the cathode. In the organic light emitting device according to the present invention, the organic compound layer includes a light emitting layer or a layer bearing a light emitting function. In addition, the phenanthrene compound according to the present invention is contained in this organic compound layer. The structure example of the organic light emitting device according to the present invention will be described below.

(i) (substrate/) anode/light emitting layer/cathode
(ii) (substrate/) anode/hole transporting layer/electron transporting layer/cathode
(iii) (substrate/) anode/hole transporting layer/light emitting layer/electron transporting layer/cathode
(iv) (substrate/) anode/hole injecting layer/hole transporting layer/light emitting layer/electron transporting layer/cathode
(v) (substrate/) anode/hole transporting layer/light emitting layer/hole/exciton blocking layer/electron transporting layer/cathode However, the organic light emitting device according to the present invention is not limited to the aspects of the above described (i) to (v). For instance, an insulation layer, an adhesive layer or an interference layer may also be provided in the interface between the electrode and the organic compound layer. In addition, the electron transporting layer or the hole transporting layer may also include two layers having different ionization potentials. Thus, the organic light emitting device according to the present invention can adopt various layer structures.

In addition, the organic light emitting device according to the present invention may be a so-called top emission type in which light is taken out from the electrode in an opposite side of the substrate, or may also be a so-called bottom emission type in which light is taken out from a substrate side. In addition, a structure also may be adopted in which light is taken out from both sides, by employing a transparent substrate as the substrate and employing a transparent electrode for the anode and the cathode.

The phenanthrene compound according to the present invention is contained in an organic compound layer constituting an organic light emitting device, specifically, a hole injecting layer, a hole transporting layer, a light emitting layer, a hole/exciton blocking layer, an electron transporting layer or an electron injecting layer. The phenanthrene compound can be contained in the light emitting layer.

In the organic light emitting device according to the present invention, the light emitting layer may include only a light emitting material, or may also include a host and a guest. The light emitting layer can include the host and the guest.

When the light emitting layer includes the host and the guest, the host is a compound which becomes a main component, among the compounds which constitute the light emitting layer, and has the largest weight ratio in all compounds which constitute the light emitting layer. In addition, the host is a compound having a function as a matrix which surrounds the periphery of the guest in the light emitting layer, and further having both functions of transporting the carrier and imparting the excitation energy to the guest, as well.

On the other hand, the guest is a compound which corresponds to an accessory component with respect to the main component (host), and is a compound which mainly has the light emitting function. The concentration of the guest contained in the light emitting layer is 0.01 wt % or more and 50 wt % or less with respect to the total amount of the material constituting the light emitting layer. The concentration can be 0.1 wt % or more and 20 wt % or less. The guest may be uniformly contained in the whole of the light emitting layer, or may also be contained so as to form a concentration gradient. It is also acceptable alternatively to make a particular region locally contain the guest and provide the region in the light emitting layer, in which the guest does not exist.

Here, when the light emitting layer includes the host and the guest, the phenanthrene compound according to the present invention can be used as the host of the light emitting layer. On the other hand, the phosphorescent light emitting material can be used as the guest with respect to this host. At this time, the emission color of the phosphorescent light emitting material is not limited in particular, but can be a green color having the maximum peak wavelength of the emitted light in the range of 500 nm or more and 530 nm or less.

When the phenanthrene compound according to the present invention is used as the host of the light emitting layer, the phosphorescent light emitting material which is the corresponding guest includes, for instance, metal complexes such as an iridium complex, a platinum complex, a rhenium complex, a copper complex, a europium complex and a ruthenium complex. Among the metal complexes, the phosphorescent light emitting material can be an iridium complex which has strong phosphorescent light emitting properties. In addition, for the purpose of assisting the transmission of the exciton or the carrier, a plurality of phosphorescent light emitting materials also may be contained in the light emitting layer.

Specific examples of the iridium complex to be used as the phosphorescent light emitting material will be described below, but the present invention is not limited to these examples.

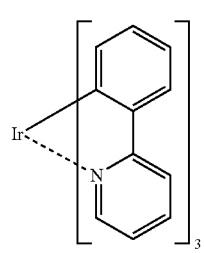
Ir-1

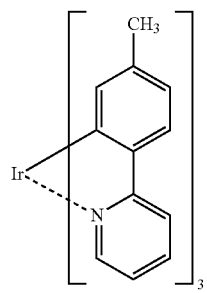
Ir-2

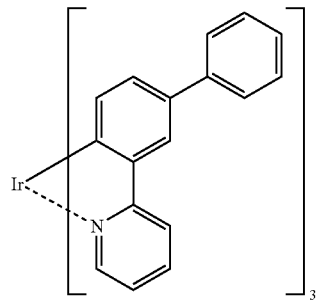
Ir-3

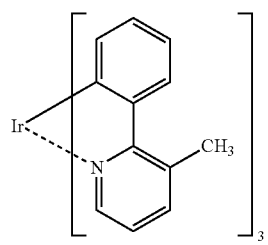
Ir-4

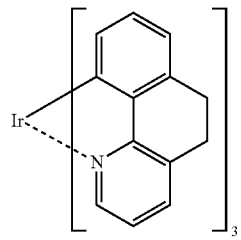
Ir-5

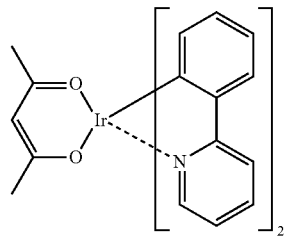
Ir-6

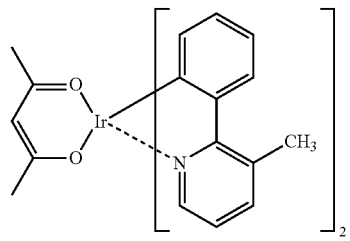
Ir-7

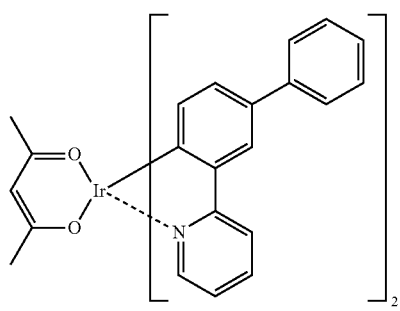
Ir-8

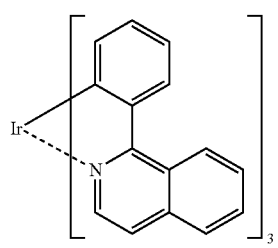
Ir-9

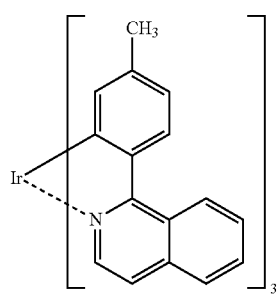
Ir-10

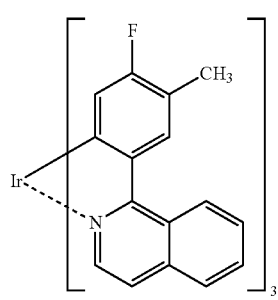
Ir-11

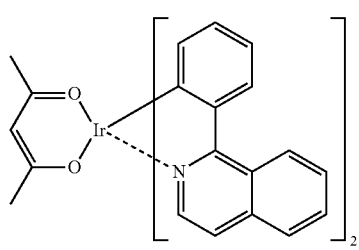
Ir-12

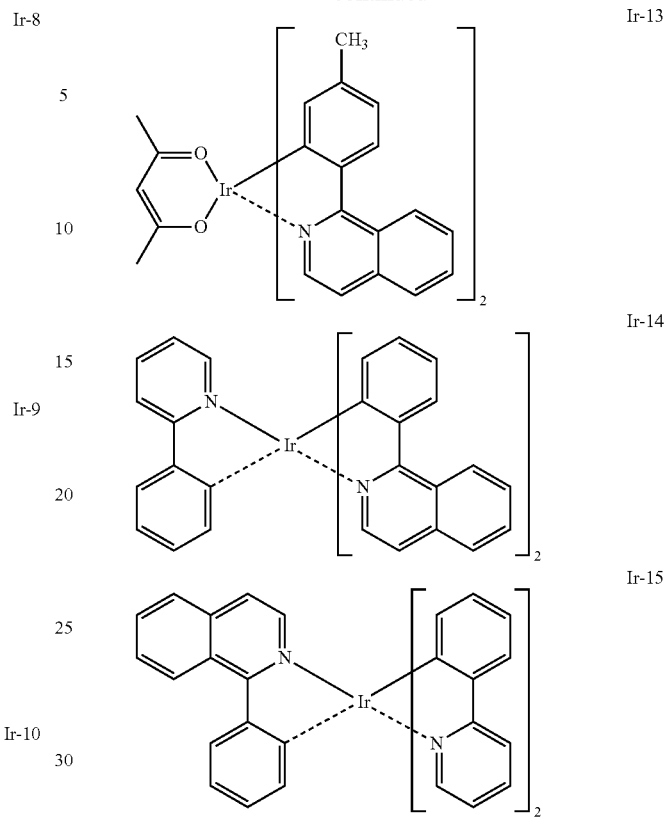

Ir-13

Ir-14

Ir-15

Here, conventionally known compounds with a low molecular weight and with a high molecular weight can be used, as needed, other than the phenanthrene compound according to the present invention. Specifically, a hole injecting/transporting compound, a host material, a light emitting compound, an electron injecting/transporting compound and the like can be used together. Examples of these compounds will be described below.

A hole injecting/transporting material can be a material which exhibits a high mobility of a hole so that a hole can be easily injected thereinto from an anode and the injected hole can be transported to a light emitting layer therethrough. A material with a low molecular weight and a material with a high molecular weight, which have hole injecting/transporting performance, include triarylamine derivatives, phenylenediamine derivatives, stilbene derivatives, phthalocyanine derivatives, porphyrin derivatives, poly(vinylcarbazole), poly(thiophene) and other electroconductive polymers.

The light emitting material which is mainly involved with a light emitting function includes condensation cyclic compounds (for instance, fluorene derivatives, naphthalene derivatives, pyrene derivatives, perylene derivatives, tetracene derivatives, anthracene derivatives and rubrene), quinacridone derivatives, coumarin derivatives, stilbene derivatives, organoaluminium complexes such as tris(8-quinolate)aluminum, organoberyllium complexes, and polymer derivatives such as poly(phenylenevinylene) derivatives, poly(fluorene) derivatives and poly(phenylene) derivatives, in addition to the above described phosphorescent light emitting guest materials and derivatives thereof.

An electron injecting/transporting material can be arbitrarily selected from substances to which an electron is easily injected from a cathode and which can transport the injected electron to the light emitting layer therethrough; and is selected in consideration of a balance with the hole mobility of the hole injecting/transporting material and the like. A material having electron injecting/transporting performance includes oxadiazole derivatives, oxazole derivatives, pyrazine derivatives, triazole derivatives, triazine derivatives, quinoline derivatives, quinoxaline derivatives, phenanthroline derivatives and organoaluminum complexes.

A material constituting an anode can have a work function as large as possible. Usable materials include, for instance: an elemental metal such as gold, platinum, silver, copper, nickel, palladium, cobalt, selenium, vanadium and tungsten; alloys formed by combining two or more of these elemental metals; and metal oxides such as tin oxide, zinc oxide, indium oxide, indium tin oxide (ITO) and indium zinc oxide. An electroconductive polymer such as polyaniline, polypyrrole and polythiophene can be also used. These electrode materials may be used each singly or in a combination of two or more of them. In addition, the anode may include one layer or a plurality of layers.

On the other hand, a material constituting a cathode can have a small work function. The material includes, for instance: an alkaline metal such as lithium, an alkaline earth metal such as calcium, and an elemental metal such as aluminum, titanium, manganese, silver, lead and chromium. Alternatively, alloys formed by combining two or more of these elemental metals can be also used. For instance, the alloys such as magnesium-silver, aluminum-lithium and aluminum-magnesium can be used. A metal oxide such as indium tin oxide (ITO) can be also used. These electrode materials may be used each singly or in a combination of two or more of them. The cathode may have a one-layer structure or may also have a multilayer structure.

In the organic light emitting device according to the present invention, a layer containing an organic compound according to the present invention and a layer formed from another organic compound are formed by the methods which will be described below. In general, a thin film is formed by a vacuum vapor-deposition method, an ionization vapor-deposition method, a sputtering method, a plasma or a known coating method (for instance, a spin coating method, a dipping method, a casting method, an LB method, an ink-jet method or the like) with the use of a solution in which the compound has been dissolved in an appropriate solvent. Here, a layer formed by a vacuum vapor-deposition method, a solution coating method or the like is difficult to crystallize and is superior in stability over time. When a film is formed by an application method, the film can be also formed using the compound in combination with an appropriate binder resin.

The above described binder resin includes a polyvinyl carbazole resin, a polycarbonate resin, a polyester resin, an ABS resin, an acrylic resin, a polyimide resin, a phenol resin, an epoxy resin, a silicone resin and a urea resin. However, the binder is not limited to these resins. In addition, these binder resins may be used each singly as a homopolymer or a copolymer, or may be used in a form of having been mixed with one or more resins. Furthermore, a well-known addition agent such as a plasticizer, an antioxidant and a UV absorber may be used together as needed.

An apparatus having an organic light emitting device according to the present embodiment will be described below.

The organic light emitting device according to the present embodiment can be used for a display unit and a lighting unit. The organic light emitting device can be used for a light source of an image forming apparatus of an electrophotographic type, the back light of a liquid crystal display unit and the like, in addition to the above units.

The display unit has an organic light emitting device according to the present embodiment provided in the display section. This display section has a plurality of pixels, this pixel has an organic light emitting device according to the present embodiment and a TFT device which is one example of a switching device, and the anode or the cathode of this organic light emitting device is connected to the drain electrode or the source electrode of the TFT device. The display unit can be used as an image display unit for a PC and the like. The display unit may also be an image input device which further has an input section for inputting image information.

The image input device has an input section for inputting image information from an area CCD, a linear CCD, a memory card and the like, and a display section for displaying the input information. If the image input device further has an image pickup optical system, the image input device becomes an imaging apparatus such as a digital camera. The display section constituting the imaging apparatus or an ink jet printer may also have both of an image output function for displaying an image based on the image information which has been input from the outside and an input function for inputting the processing information into the image as an operation panel. The display unit may also be used for the display section of a multifunctional printer.

FIGURE is schematic sectional view illustrating an example of a display unit using an organic light emitting device according to the present invention. As for a display unit 1 in FIGURE, 2 sets of combinations of an organic light emitting device and a TFT device are illustrated. In addition, the display unit may further have a transistor for controlling light emission intensity, though the transistor is not shown. The display unit 1 in FIGURE displays an image by turning on or off the organic light emitting device by driving the switching device according to the information, and conveys the information. The details of the structure will be described below.

The display unit 1 in FIGURE has a substrate 11 of glass or the like, and a moisture-proof film 12 for protecting a TFT device or an organic compound layer provided in the upper part of the substrate 11. A reference numeral 13 is a metallic gate electrode 13. A reference numeral 14 is a gate insulation film, and a reference numeral 15 is a semiconductor layer.

A TFT device 18 has a semiconductor layer 15, a drain electrode 16 and a source electrode 17. An insulation film 19 is provided in the upper part of the TFT device 18. An anode 21 of the organic light emitting device is connected to the source electrode 17 through a contact hole 20. The display unit is not limited to this structure, but any one of the anode and the cathode may be connected to any one of the source electrode and the drain electrode of the TFT device.

In addition, in the display unit 1 in FIGURE, an organic compound layer 22 is illustrated as a single layer. However, in the present invention, the organic compound layer 22 is not limited to the single layer, but may also be a layered product formed of a plurality of layers. In addition, a first protective layer 24 and a second protective layer 25 which suppress the degradation of the organic light emitting device are provided on the cathode 23.

EXAMPLES

Example 1

Synthesis of Exemplified Compound A04

(1) Synthesis of 2-Chlorophenanthrene

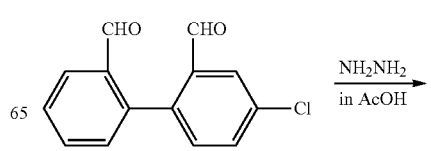

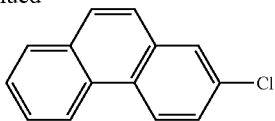

A reagent and a solvent shown below were charged into a 500 mL three-neck flask provided with a dropping funnel.
4-Chloro-2,2'-diformyl biphenyl: 5.33 g (21.8 mmol)
Acetic acid: 250 mL Next, the reaction solution was heated and refluxed while being stirred under nitrogen, and a solution in which 30 mL of acetic acid and 1.42 g (28.4 mmol) of hydrazine monohydrate had been mixed was slowly added dropwise thereto through the dropping funnel for 45 minutes. After the dropwise addition was finished, the reaction solution was continually heated and refluxed further for 4 hours. After the reaction was finished, 100 mL of water was added into the reaction solution while the mixed solution was stirred, and the precipitated product was filtered out. Next, 3.24 g of 2-chlorophenanthrene (yield of 70%) was obtained by heating, dispersing and washing this product in a methanol/acetone mixture solvent to purify the product.

(2) Synthesis of Exemplified Compound A04

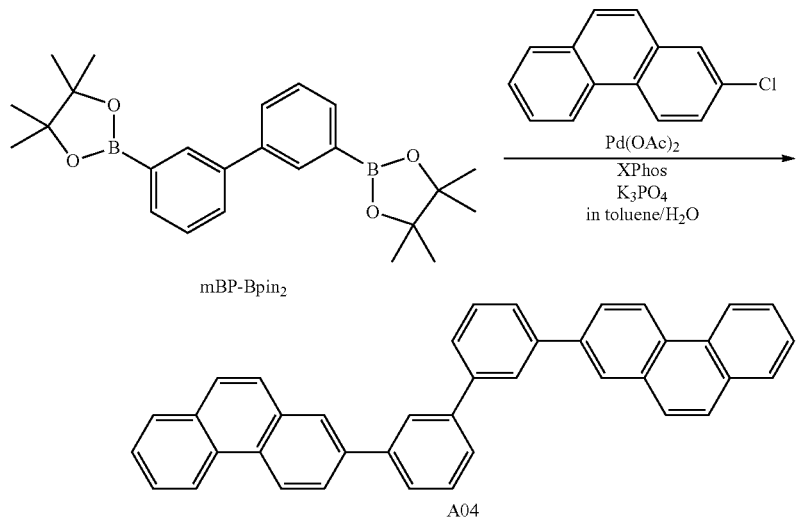

A reagent and a solvent shown below were charged into a 200 mL recovery flask.
mBP-Bpin$_2$ (boronic acid ester): 1.50 g (3.69 mmol)
2-Chlorophenanthrene: 1.65 g (7.76 mmol)
Palladium acetate: 83 mg (0.37 mmol)
XPhos (2-dicyclohexyl phosphino-2',4',6'-triisopropyl biphenyl): 528 mg (1.11 mmol)
Potassium phosphate: 2.35 g (11.1 mmol)
Toluene: 80 mL
Water: 2 mL Next, this reaction solution was stirred at 100° C. under nitrogen for 10 hours. After the reaction was finished, water was added into the reaction solution, the resultant solution was stirred, and the precipitated crystal was filtered out. Next, this crystal was washed successively with water, ethanol and acetone, and a crude product was obtained. Next, this crude product was heated and dissolved in toluene, the hot solution was filtrated, and the filtrate was recrystallized twice by using a chlorobenzene solvent. Next, the obtained crystal was dried at 150° C. in a vacuum and was purified by sublimation on conditions of $1 \times 10^{-4}$ Pa and 350° C. Thereby, 777 mg of a high-purity exemplified compound A04 was obtained (yield of 42%).

The result of having identified the obtained compound is shown below.

[MALDI-TOF-MS (Matrix-Assisted Laser Desorption/Ionization Time-of-Flight Mass Spectrometry)]
observed: m/z=506.34, calcd.: $C_{40}H_{26}$=506.20

[$^1$H-NMR (400 MHz, CDCl$_3$)]
δ 8.79 (d, 2H), 8.73 (d, 2H), 8.19 (d, 2H), 8.08 (s, 2H), 8.01 (dd, 2H), 7.92 (d, 2H), 7.90-7.60 (m, 14H).

In addition, physical properties of the exemplified compound A04 were measured and evaluated according to the following methods.

(1) Triplet Exciton Energy (T$_1$ Energy)

After a diluted solution of the exemplified compound A04 by toluene was prepared, this diluted solution was subjected to the measurement of a phosphorescent spectrum under argon atmosphere on conditions of 77 K and an excitation wavelength of 350 nm. The T$_1$ energy was obtained from the peak wavelength of the first light-emission peak in the obtained phosphorescent spectrum. As a result, the T$_1$ energy was 466 nm in terms of a wavelength value.

(2) Energy Gap

A thin film of the exemplified compound A04 for measurement was formed on a glass substrate by heating and vapor deposition. At this time, the thickness of the thin film for measurement was set at 20 nm. Next, the above described thin film for measurement was measured for a light-absorption spectrum with an ultraviolet spectrophotometer (V-560 made by JASCO Corporation). The energy gap was determined from the absorption edge of the obtained light-absorption spectrum. As a result, the absorption edge of the light-absorption spectrum was 347 nm, and the energy gap of the exemplified compound A04 was 3.57 eV.

(3) Ionization Potential

Ionization potential was measured by using the above described thin film for measurement, which was used for the measurement of the energy gap, with a photoelectron spectrometer AC-3 (manufactured by Riken Keiki Co., Ltd.). As a result of the measurement, the ionization potential of the exemplified compound A04 was 6.43 eV.

(4) LUMO Level

The LUMO level can be estimated from the difference between the ionization potential value and the energy gap value. Here, the LUMO level in the exemplified compound A04 was −2.86 eV.

Example 2

Synthesis of Exemplified Compound A09

(1) Synthesis of Intermediate Product PT-Bpin

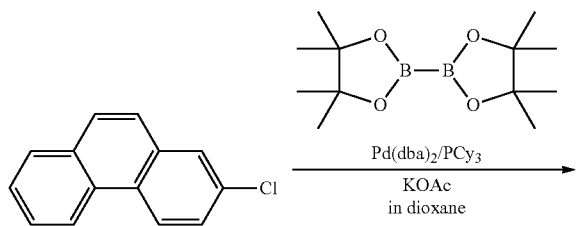

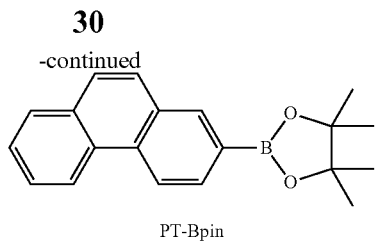

PT-Bpin

A reagent and a solvent shown below were charged into a 300 mL recovery flask.

2-Chlorophenanthrene: 3.00 g (14.1 mmol)
Bis(pinacolato)diboron: 4.30 g (16.9 mmol)
Bis(dibenzylideneacetone)palladium(0): 406 mg (0.71 mmol)
Tricyclohexyl phosphine: 593 mg (2.12 mmol)
Potassium acetate: 2.77 g (28.2 mmol)
1,4-Dioxane: 100 mL Next, this reaction solution was stirred at 95° C. under nitrogen for 7 hours. After the reaction was finished, the reaction solution was washed with water and was dried on sodium sulfate, then the resultant solution was concentrated under reduced pressure, and thereby a crude product was obtained. Next, this crude product was purified with a silica gel column chromatography (eluent: heptane/toluene=1/1), and thereby 3.23 g of an intermediate product PT-Bpin was obtained (yield of 75%).

(2) Synthesis of Exemplified Compound A09

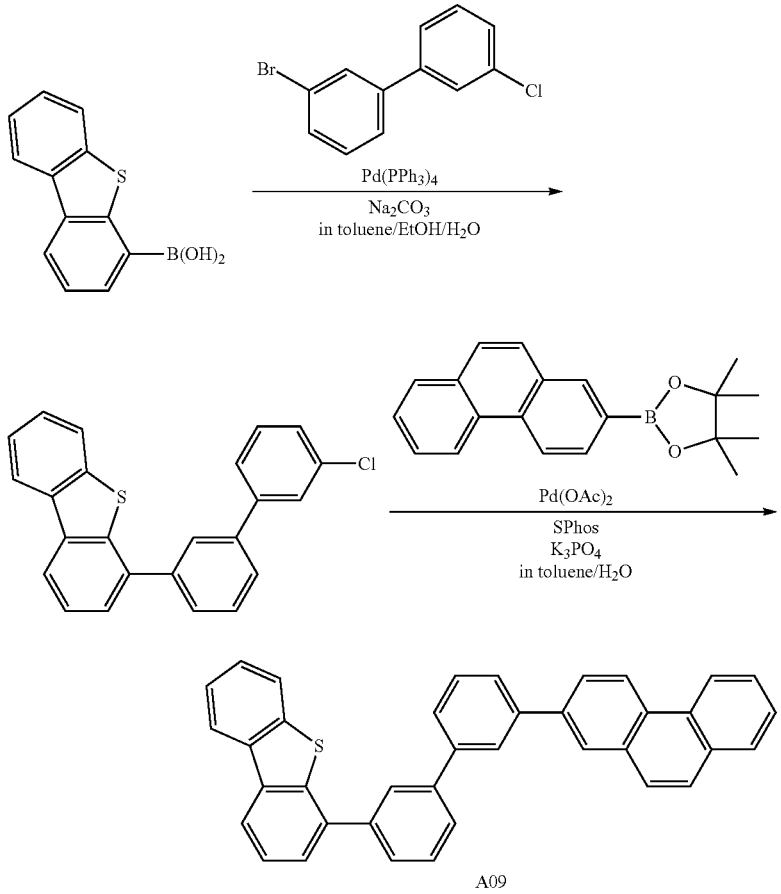

A09

A reagent and a solvent shown below were charged into a 200 mL recovery flask.

3-Bromo-3'-chloro biphenyl: 3.00 g (11.2 mmol)
4-Dibenzothiophene boronate: 2.63 g (11.6 mmol)
Tetrakis(triphenyl phosphine)palladium(0): 352 mg (0.31 mmol)
Toluene: 60 mL
Ethanol: 30 mL
10 wt % sodium carbonate aqueous solution: 30 mL Next, this reaction solution was heated and refluxed while being stirred under nitrogen for 5 hours. After the reaction was finished, the reaction solution was washed with water and was dried on sodium sulfate, then the resultant solution was concentrated under reduced pressure, and thereby a crude product was obtained. Next, this crude product was purified with a silica gel column chromatography (eluent: heptane), and thereby 3.75 g of 4-(3'-chlorobiphenyl-3-yl)dibenzothiophene was obtained (yield of 90%).

Subsequently, a reagent and a solvent shown below were charged into a 50 mL recovery flask.

PT-Bpin: 583 mg (1.92 mmol)
4-(3'-Chlorobiphenyl 3-yl)dibenzothiophene: 646 mg (1.74 mmol)
Palladium acetate: 24 mg (0.11 mmol)
SPhos (2-dicyclohexylphosphino-2',6'-dimethoxybiphenyl): 130 mg (0.32 mmol)
Potassium phosphate: 1.11 g (5.23 mmol)
Toluene: 25 mL
Water: 0.6 mL Next, this reaction solution was stirred at 100° C. under nitrogen for nine and a half hours. After the reaction was finished, the reaction solution was washed with water and was dried on sodium sulfate, then the resultant solution was concentrated under reduced pressure, and thereby a crude product was obtained. Next, this crude product was purified with a silica gel column chromatography (eluent: heptane/chloroform=3/1), and then was recrystallized from a toluene/octane mixture solvent. Next, the obtained crystal was dried at 150° C. in a vacuum and was purified by sublimation on conditions of 1×10⁻⁴ Pa and 330° C. Thereby, 360 mg of a high-purity exemplified compound A09 was obtained (yield of 40%).

The result of having identified the obtained compound is shown below.

[MALDI-TOF-MS]
observed: m/z=512.30, calcd.: $C_{38}H_{24}S$=512.16
[$^1$H-NMR (400 MHz, $CDCl_3$)]
δ 8.77 (d, 1H), 8.72 (d, 1H), 8.30-8.15 (m, 3H), 8.09 (d, 2H), 7.98 (dd, 1H), 7.91 (d, 1H), 7.88-7.55 (m, 13H), 7.48 (m, 2H).

The exemplified compound A09 was evaluated for the $T_1$ energy, the energy gap, the ionization potential and the LUMO level with a similar method to that in Example 1. As a result, the $T_1$ energy was 466 nm, the energy gap was 3.43 eV (absorption edge: 361 nm), the ionization potential was 6.36 eV and the LUMO level was −2.93 eV.

Example 3

Synthesis of Exemplified Compound B08

(1) Synthesis of Intermediate Product MePT-Bpin

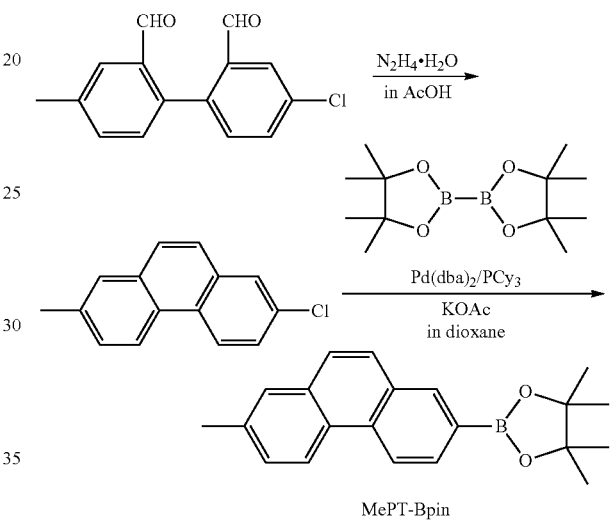

MePT-Bpin

First, 2-chloro-7-methyl phenanthrene was synthesized by using 4-chloro-4'-methyl-2,2'-diformyl biphenyl as a starting material, with a similar method to that in Example 1 (1). Next, MePT-Bpin was synthesized from 2-chloro-7-methyl phenanthrene with a similar method to that in Example 2 (1).

(2) Synthesis of Exemplified Compound B08

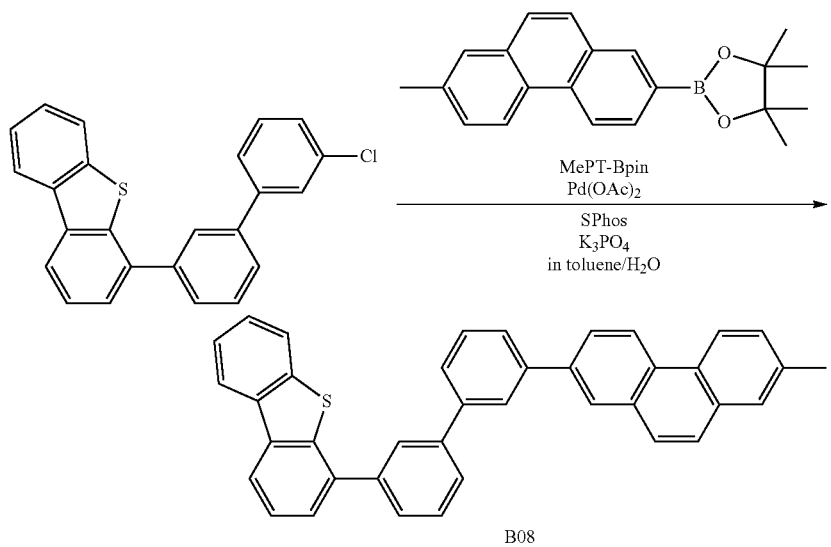

B08

A reagent and a solvent shown below were charged into a 50 mL recovery flask.
MePT-Bpin: 440 mg (1.38 mmol)
4-(3'-chlorobiphenyl-3-yl)dibenzothiophene: 394 mg (1.06 mmol)
Palladium acetate: 14 mg (0.062 mmol)
SPhos (2-dicyclohexylphosphino-2',6'-dimethoxybiphenyl): 78 mg (0.19 mmol)
Potassium phosphate: 675 mg (3.18 mmol)
Toluene: 18 mL
Water: 0.4 mL Next, this reaction solution was stirred at 100° C. under nitrogen for 10 hours. After the reaction was finished, the reaction solution was washed with water and was dried on sodium sulfate, then the resultant solution was concentrated under reduced pressure, and thereby a crude product was obtained. Next, this crude product was purified with a silica gel column chromatography (eluent: heptane/chloroform=3/1), and then was recrystallized from a toluene/octane mixture solvent. Next, the obtained crystal was dried at 150° C. in a vacuum and was purified by sublimation on conditions of $1 \times 10^{-4}$ Pa and 340° C. Thereby, 257 mg of a high-purity exemplified compound B08 was obtained (yield of 46%).

The obtained compound was identified by mass spectroscopy.
[MALDI-TOF-MS]
observed: m/z=526.37, calcd.: $C_{39}H_{26}S$=526.18

The exemplified compound B08 was evaluated for the $T_1$ energy, the energy gap, the ionization potential and the LUMO level with a similar method to that in Example 1. As a result, the $T_1$ energy was 468 nm, the energy gap was 3.43 eV (absorption edge: 362 nm), the ionization potential was 6.29 eV and the LUMO level was −2.86 eV.

Comparative Examples 1 to 5

Comparison compounds H01 to H05 shown below were evaluated for the $T_1$ energy and the LUMO level with a similar method to that in Example 1. The results are shown in Table 3. The results are shown together with the results of Examples 1 to 3 in Table 3.

H01

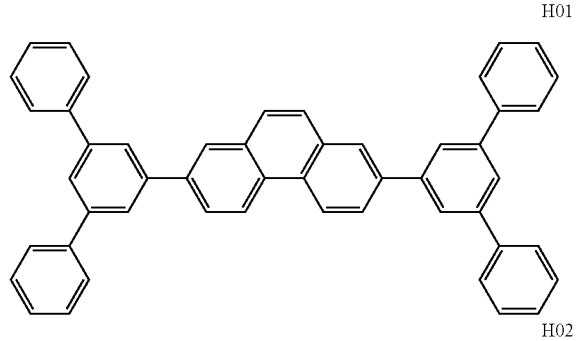

H02

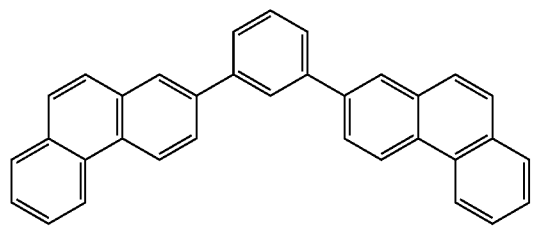

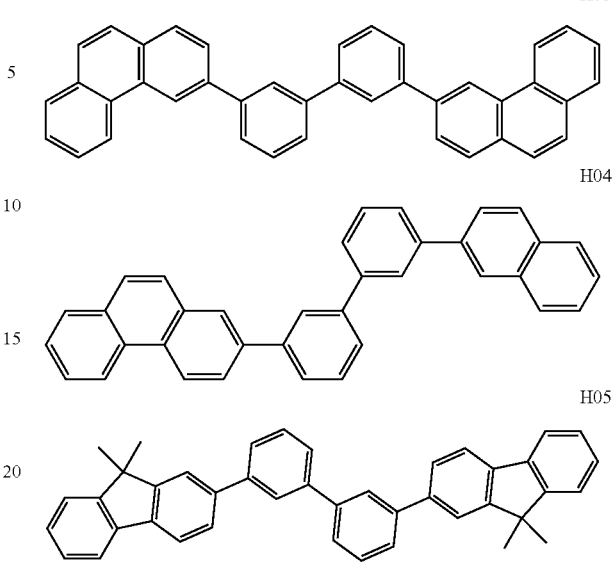

TABLE 3

| | | $T_1$ [nm] | LUMO[Note 1] [eV] |
|---|---|---|---|
| Example 1 | Exemplified compound A04 | 466 | −2.86 |
| Example 2 | Exemplified compound A09 | 466 | −2.93 |
| Example 3 | Exemplified compound B08 | 468 | −2.86 |
| Comparative Example 1 | Compound H01 | 480 | −2.82 |
| Comparative Example 2 | Compound H02 | 467 | −2.69 |
| Comparative Example 3 | Compound H03 | 493 | −2.72 |
| Comparative Example 4 | Compound H04 | 490 | −2.81 |
| Comparative Example 5 | Compound H05 | 481 | −2.74 |

[Note 1]ESTIMATED VALUE

It is understood from Table 3 that the phenanthrene compounds according to the present invention have higher $T_1$ energy and a deeper LUMO level (larger absolute value of LUMO level).

Here, the exemplified compound A04 has higher $T_1$ energy than the compound H01. This difference is considered to come from a difference in the number of the aryl groups by which the phenanthrene ring is substituted. In other words, the exemplified compound A04 has a fewer number of aryl groups by which the phenanthrene ring is substituted than the compound H01 (exemplified compound A04: 1 group, and compound H01: 2 groups), and accordingly has higher $T_1$ energy.

In addition, the exemplified compound A04 has a deeper LUMO level than the compound H02. This is caused by that two phenanthrene skeletons are linked by a linking group which makes the LUMO level deeper. Specifically, the two phenanthrene skeletons are linked by an m-biphenylene linking group which makes the LUMO level deeper than an m-phenylene linking group, and thereby the LUMO level of the whole compound is more deepened.

In addition, the exemplified compound A04 has higher $T_1$ energy than the compound H03. This comes from the difference between the linkage positions at which the phenanthrene ring is linked with the m-biphenylene linking group. In other words, the exemplified compound A04 in which the 2-position of the phenanthrene ring is the linkage position with the m-biphenylene linking group has the higher $T_1$ energy than the compound H03 in which the 3-position of the phenanthrene ring is the linkage position with the m-biphenylene linking group.

In addition, the exemplified compound A04 has higher $T_1$ energy than the compound H04. The compound H04 is a compound in which one of two phenanthrene skeletons constituting the exemplified compound A04 has been changed to a naphthalene skeleton. Here, the naphthalene skeleton has lower $T_1$ energy than the phenanthrene skeleton, and accordingly the $T_1$ energy of the whole compound H04 becomes lower than that of the whole exemplified compound A04.

In addition, the exemplified compound A04 has a deeper LUMO level than the compound H05. Both of the compounds have such different points from each other that condensed rings linked by the m-biphenylene linking group are different from each other (phenanthrene ring and fluorene ring). Here, according to Table 1, the phenanthrene ring has a deeper LUMO level than the fluorene ring, and accordingly, the exemplified compound A04 similarly has a deeper LUMO level than the compound H05.

Example 4

An organic light emitting device in which anode/hole transporting layer/light emitting layer/hole blocking layer/electron transporting layer/cathode were provided on a substrate in this order was produced with the method described below. One part of compounds used in the present example will be shown below.

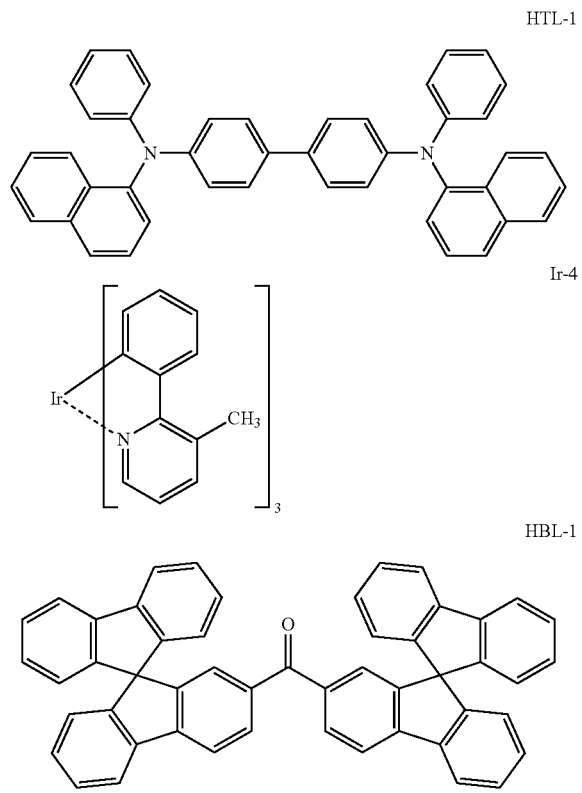

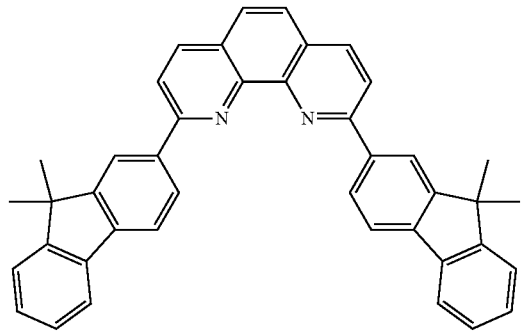

An anode was produced by forming a film of ITO on a glass substrate with a sputtering method. The film thickness of the anode at this time was controlled to 120 nm. The substrate thus having the ITO film formed thereon was used as a transparent electroconductive support substrate (ITO substrate) in a later step. Next, films of an organic compound layer and an electrode layer shown in Table 4 were continuously formed on the anode with a vacuum vapor-deposition method using resistance heating. The pressure in the vacuum chamber at this time was set at $1\times10^{-5}$ Pa, and the films were produced so that the area of the electrodes which confront each other was 3 mm$^2$.

TABLE 4

|  | Constituent material | Film thickness [nm] |
| --- | --- | --- |
| Hole transporting layer | HTL-1 | 40 |
| Light emitting layer | Host: exemplified compound A04 Guest: Ir-4 (Host:guest = 85:15 (weight ratio)) | 30 |
| Hole blocking layer | HBL-1 | 10 |
| Electron transporting layer | ETL-1 | 30 |
| First metal electrode layer | LiF | 0.5 |
| Second metal electrode layer | Al | 100 |

Next, the organic light emitting device was covered with glass plates for protection in a dried air atmosphere and was sealed with an acrylic-resin-based adhesive so that the organic light emitting device did not degrade due to the adsorption of moisture. The organic light emitting device was obtained in the above described way.

The ITO electrode in the obtained organic light emitting device was set at a positive electrode, the Al electrode was set at a negative electrode, and an application voltage of 4.9 V was applied between the electrodes. As a result, a green light emission with a luminous efficiency of 67.5 cd/A, an external quantum efficiency of 18.1%, and a luminance of 2,000 cd/m$^2$ was observed. In addition, the CIE chromaticity coordinate in this device was (x, y)=(0.35, 0.61). Furthermore, in this light emitting device, the luminance half-life at a constant current density of 100 mA/cm$^2$ was 110 hours.

Example 5

A device was produced with a similar method to that in Example 4, except that the exemplified compound A09 was used as the host of the light emitting layer, in place of the exemplified compound A04 in Example 4. The obtained device was evaluated with a similar method to that in Example 4. The results are shown in Table 5.

Example 6

A device was produced with a similar method to that in Example 4, except that the exemplified compound B08 was used as the host of the light emitting layer, in place of the exemplified compound A04 in Example 4. The obtained device was evaluated with a similar method to that in Example 4. The results are shown in Table 5.

Comparative Example 6

A device was produced with a similar method to that in Example 4, except that the exemplified compound H02 was used as the host of the light emitting layer, in place of the exemplified compound A04 in Example 4. The obtained device was evaluated with a similar method to that in Example 4. The results are shown in Table 5.

Comparative Example 7

A device was produced with a similar method to that in Example 4, except that the exemplified compound H03 was used as the host of the light emitting layer, in place of the exemplified compound A04 in Example 4. The obtained device was evaluated with a similar method to that in Example 4. The results are shown in Table 5.

Comparative Example 8

A device was produced with a similar method to that in Example 4, except that the exemplified compound H05 was used as the host of the light emitting layer in place of the exemplified compound A04 in Example 4. The obtained device was evaluated with a similar method to that in Example 4. The results are shown in Table 5.

TABLE 5

| | | @2000 cd/m² | | | |
| --- | --- | --- | --- | --- | --- |
| | Host | CIE chromaticity | Applied voltage [V] | Luminous efficiency [cd/A] | External quantum yield [%] | Luminance half-life (@100 mA/cm²) [hr] |
| Example 4 | A04 | (0.35, 0.61) | 4.9 | 67.5 | 18.1 | 110 |
| Example 5 | A09 | (0.34, 0.62) | 4.9 | 69.1 | 18.5 | 385 |
| Example 6 | B08 | (0.33, 0.62) | 5.0 | 68.9 | 18.4 | 323 |
| Comparative Example 6 | H02 | (0.35, 0.61) | 5.4 | 61.2 | 16.8 | 77 |
| Comparative Example 7 | H03 | (0.35, 0.62) | 4.9 | 51.5 | 13.8 | 85 |
| Comparative Example 8 | H05 | (0.33, 0.63) | 5.1 | 58.7 | 15.7 | 100 |

From the above description, the phenanthrene compound according to the present invention is a new compound having high $T_1$ energy and a deep LUMO level. The light emitting device having enhanced light emission efficiency is obtained by using the phenanthrene compound according to the present invention as the host of the light emitting layer constituting the organic light emitting device.

REFERENCE SIGNS LIST

18: TFT device, 21: Anode, 22: Organic compound layer, and 23: Cathode While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-248352, filed Nov. 5, 2010, which is hereby incorporated by reference herein in its entirety.

The invention claimed is:

1. A phenanthrene compound represented by the following general formula [1]:

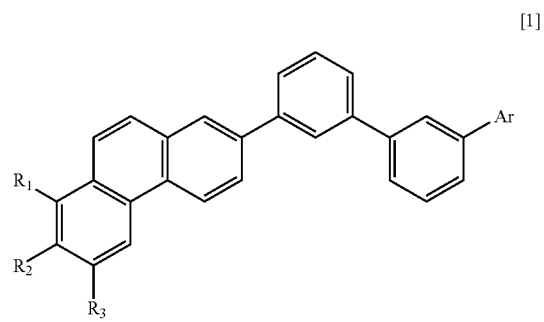

[1]

wherein $R_1$ to $R_3$ each represent a hydrogen atom or an alkyl group having 1 to 4 carbon atoms; and Ar is a substituent selected from any in the group consisting of aryl groups represented by the following formulae [2a] to [2h]:

[2a]

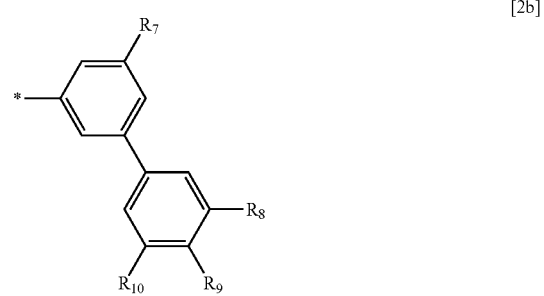

[2b]

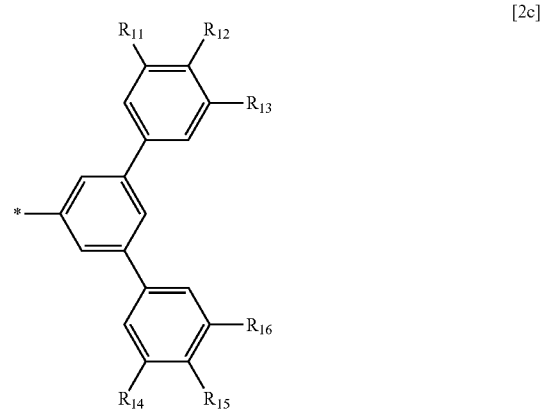

[2c]

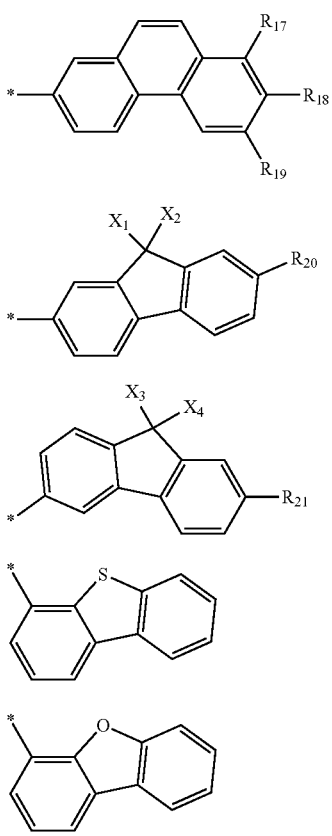

wherein in formulae [2a] to [2f], $R_4$ to $R_{21}$ each represent a hydrogen atom or an alkyl group having 1 to 4 carbon atoms; in formulae [2e] and [2f], $X_1$ to $X_4$ each represent a hydrogen atom or an alkyl group having 1 to 4 carbon atoms; and in formulae [2a] to [2h], * represents a bond.

2. The phenanthrene compound according to claim 1, wherein each of $R_1$ to $R_{21}$ is a hydrogen atom.

3. An organic light emitting device comprising an anode, a cathode and an organic compound layer which is sandwiched between the anode and the cathode, wherein the organic compound layer contains the phenanthrene compound according to claim 1.

4. The organic light emitting device according to claim 3, wherein the phenanthrene compound is contained in a light emitting layer.

5. The organic light emitting device according to claim 4, wherein the light emitting layer comprises a host and a guest, and the host is the phenanthrene compound.

6. The organic light emitting device according to claim 5, wherein the guest is a phosphorescent light emitting material.

7. The organic light emitting device according to claim 6, wherein the phosphorescent light emitting material is an iridium complex.

8. A display unit having the organic light emitting device according to claim 3 and a switching device connected to the organic light emitting device.

9. An image input device having a display section for displaying an image and an input section for inputting image information, wherein the display section has a plurality of pixels, and the plurality of pixels has the organic light emitting device according to claim 3 and a switching device connected to the organic light emitting device.

10. A device comprising a substrate and the organic light emitting device according to claim 3.

* * * * *